(12) United States Patent
Leibel (10) Patent No.: US 9,078,758 B2
(45) Date of Patent: Jul. 14, 2015

(54) WRIST IMPLANT FOR CARPAL HEMIARTHROPLASTY

(75) Inventor: David A. Leibel, Princeton, MN (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 14/116,977

(22) PCT Filed: May 10, 2012

(86) PCT No.: PCT/US2012/037248
§ 371 (c)(1),
(2), (4) Date: Dec. 6, 2013

(87) PCT Pub. No.: WO2012/154920
PCT Pub. Date: Nov. 15, 2012

(65) Prior Publication Data
US 2014/0100664 A1 Apr. 10, 2014

Related U.S. Application Data

(60) Provisional application No. 61/485,447, filed on May 12, 2011.

(51) Int. Cl.
*A61F 2/42* (2006.01)
*A61B 17/86* (2006.01)
*A61F 2/30* (2006.01)

(52) U.S. Cl.
CPC ............ *A61F 2/4261* (2013.01); *A61B 17/86* (2013.01); *A61F 2002/305* (2013.01);

(Continued)

(58) Field of Classification Search
CPC ............... A61F 2/4261; A61F 2/4241; A61F 2002/4264; A61F 2/4262; A61F 2002/4287
USPC ........................................... 623/21.11–21.14
See application file for complete search history.

(56) References Cited

U.S. PATENT DOCUMENTS 2,924,276 A 2/1960 Heilman et al.
3,506,982 A 4/1970 Steffee (Continued)

FOREIGN PATENT DOCUMENTS

DE 25900476 U1 9/1995
DE 10043107 C1 9/2002

(Continued)

OTHER PUBLICATIONS

International Search Report and Written Opinion for International Application No. PCT/US12/37248 mailed Aug. 31, 2012.

(Continued)

*Primary Examiner* — Bruce E Snow
*Assistant Examiner* — Brian Dukert
(74) *Attorney, Agent, or Firm* — Lerner, David, Littenberg, Krumholz & Mentlik, LLP (57) ABSTRACT

An implant for carpal hemiarthroplasty includes an articular component having a convex articular surface shaped to generally conform to an unresected distal end of a radius bone. A bearing component is rigidly fixed to the articular component opposite the convex articular surface and has a bearing surface. A carpal plate is rotatably attachable to the bearing component and has a proximal surface and a distal surface. The proximal surface has a contour that substantially conforms to the bearing surface.

14 Claims, 8 Drawing Sheets

(52) U.S. Cl.
CPC .......... *A61F 2002/30253* (2013.01); *A61F 2002/30354* (2013.01); *A61F 2002/30369* (2013.01); *A61F 2002/30378* (2013.01); *A61F 2002/30897* (2013.01); *A61F 2002/4287* (2013.01)

(56) References Cited

U.S. PATENT DOCUMENTS

| | | |
|---|---|---|
| 3,593,342 A | 7/1971 | Niebauer et al. |
| 3,745,590 A | 7/1973 | Stubstad |
| 3,837,008 A | 9/1974 | Bahler |
| 3,909,853 A | 10/1975 | Lennox |
| 3,924,276 A | 12/1975 | Eaton |
| 4,003,096 A | 1/1977 | Frey |
| 4,040,130 A | 8/1977 | Laure |
| 4,063,314 A | 12/1977 | Loda |
| 4,100,626 A | 7/1978 | White |
| 4,106,128 A | 8/1978 | Greenwald |
| 4,178,640 A | 12/1979 | Buechler et al. |
| 4,180,871 A | 1/1980 | Hamas |
| 4,183,104 A | 1/1980 | Frey |
| 4,229,840 A | 10/1980 | Gristina |
| 4,229,841 A | 10/1980 | Youm et al. |
| 4,242,759 A | 1/1981 | White |
| 4,259,752 A | 4/1981 | Taleisnik |
| 4,307,473 A | 12/1981 | Weber |
| 4,645,505 A | 2/1987 | Swanson |
| 4,714,476 A | 12/1987 | Ranawat et al. |
| 4,784,661 A | 11/1988 | Beckenbaugh |
| 4,865,605 A | 9/1989 | Dines et al. |
| 4,936,854 A | 6/1990 | Swanson |
| 5,080,673 A | 1/1992 | Burkhead et al. |
| 5,108,444 A | 4/1992 | Branemark |
| 5,135,529 A | 8/1992 | Paxson et al. |
| 5,314,485 A | 5/1994 | Judet |
| 5,326,364 A | 7/1994 | Clift, Jr. |
| 5,358,526 A | 10/1994 | Tornier |
| 5,413,609 A | 5/1995 | Nicol |
| 5,458,646 A | 10/1995 | Giachino |
| 5,489,309 A | 2/1996 | Lackey et al. |
| 5,507,821 A | 4/1996 | Sennwald |
| 5,522,900 A | 6/1996 | Hollister |
| 5,527,342 A | 6/1996 | Pietrzak et al. |
| 5,549,690 A | 8/1996 | Hollister |
| 5,549,701 A | 8/1996 | Mikhail |
| 5,593,448 A | 1/1997 | Dong |
| 5,702,447 A | 12/1997 | Walch et al. |
| 5,702,470 A | 12/1997 | Menon |
| 5,702,486 A | 12/1997 | Craig et al. |
| 5,725,585 A | 3/1998 | Zobel |
| 5,741,335 A | 4/1998 | Gerber |
| 5,766,258 A | 6/1998 | Simmen |
| 5,782,926 A | 7/1998 | Lamprecht |
| 5,800,551 A | 9/1998 | Williamson |
| 5,824,106 A | 10/1998 | Fournol |
| 5,853,413 A | 12/1998 | Carter |
| 5,879,395 A | 3/1999 | Tornier et al. |
| 5,906,210 A | 5/1999 | Herbert |
| 6,051,751 A | 4/2000 | Sioshansi |
| 6,059,832 A | 5/2000 | Menon |
| 6,126,690 A | 10/2000 | Ateshian et al. |
| 6,127,596 A | 10/2000 | Brown et al. |
| 6,159,247 A | 12/2000 | Klawitter |
| 6,168,630 B1 | 1/2001 | Keller |
| 6,221,073 B1 | 4/2001 | Weiss |
| 6,228,119 B1 | 5/2001 | Ondrla et al. |
| 6,302,915 B1 | 10/2001 | Cooney, III et al. |
| 6,352,560 B1 | 3/2002 | Poeschmann et al. |
| 6,454,808 B1 | 9/2002 | Masada |
| 6,485,520 B1 | 11/2002 | Hubach |
| 6,514,287 B2 | 2/2003 | Ondrla |
| RE38,409 E | 1/2004 | Noiles |
| 6,679,916 B1 | 1/2004 | Frankle et al. |
| 6,746,486 B1 | 6/2004 | Shultz |
| 6,790,228 B2 | 9/2004 | Hossainy |
| 6,790,234 B1 | 9/2004 | Frankle |
| 6,814,757 B2 | 11/2004 | Kopylov |
| 6,827,741 B2 | 12/2004 | Reeder |
| 6,860,902 B2 | 3/2005 | Reiley |
| 6,887,277 B2 | 5/2005 | Rauscher |
| 6,890,358 B2 | 5/2005 | Ball et al. |
| 6,969,407 B2 | 11/2005 | Klotz et al. |
| 6,986,790 B2 | 1/2006 | Ball |
| 7,160,329 B2 | 1/2007 | Cooney, III |
| 7,160,331 B2 | 1/2007 | Cooney, III |
| 7,169,184 B2 | 1/2007 | Dalla Pria |
| 7,241,314 B1 | 7/2007 | Winslow |
| 7,531,003 B2 | 5/2009 | Reindel |
| 7,608,109 B2 | 10/2009 | Dalla Pria |
| 7,625,408 B2 * | 12/2009 | Gupta et al. ............ 623/21.11 |
| 7,628,819 B2 | 12/2009 | Gupta |
| 7,708,781 B2 | 5/2010 | Scheker |
| 7,766,970 B2 | 8/2010 | Shultz et al. |
| 7,819,923 B2 | 10/2010 | Stone et al. |
| 7,837,736 B2 | 11/2010 | Bonutti |
| 7,914,583 B2 | 3/2011 | Wolfe |
| 7,918,894 B2 | 4/2011 | Wolfe |
| 8,052,757 B1 | 11/2011 | Scheker |
| 8,070,820 B2 | 12/2011 | Winslow |
| 8,118,876 B2 | 2/2012 | Gupta |
| 8,152,854 B2 | 4/2012 | Imbriglia et al. |
| 8,333,806 B2 | 12/2012 | Scheker |
| 8,454,808 B2 | 6/2013 | Owens |
| 2001/0011192 A1 | 8/2001 | Ondrla |
| 2001/0025199 A1 | 9/2001 | Rauscher |
| 2002/0055785 A1 | 5/2002 | Harris |
| 2002/0082705 A1 | 6/2002 | Bouman et al. |
| 2003/0135280 A1 | 7/2003 | Kopylov et al. |
| 2003/0187511 A1 | 10/2003 | Ball et al. |
| 2003/0216813 A1 | 11/2003 | Ball |
| 2004/0117025 A1 | 6/2004 | Reindel |
| 2004/0138756 A1 | 7/2004 | Reeder |
| 2004/0220673 A1 | 11/2004 | Pria |
| 2004/0220674 A1 | 11/2004 | Pria |
| 2004/0220678 A1 | 11/2004 | Chow et al. |
| 2004/0230312 A1 | 11/2004 | Hanson et al. |
| 2005/0004675 A1 | 1/2005 | Shultz et al. |
| 2005/0049710 A1 | 3/2005 | O'Driscoll |
| 2005/0085921 A1 | 4/2005 | Gupta |
| 2005/0171613 A1 | 8/2005 | Sartorius |
| 2006/0004462 A1 | 1/2006 | Gupta |
| 2006/0020344 A1 | 1/2006 | Shultz |
| 2006/0030946 A1 | 2/2006 | Ball |
| 2006/0036330 A1 | 2/2006 | Shultz et al. |
| 2006/0052725 A1 | 3/2006 | Santilli |
| 2006/0069446 A1 | 3/2006 | Ragusa et al. |
| 2006/0161260 A1 | 7/2006 | Thomas |
| 2006/0200248 A1 | 9/2006 | Beguin et al. |
| 2007/0055381 A1 | 3/2007 | Berelsman et al. |
| 2007/0073409 A1 | 3/2007 | Cooney, III |
| 2007/0100458 A1 | 5/2007 | Dalla Pria |
| 2007/0142919 A1 | 6/2007 | Cooney, III |
| 2007/0185582 A1 | 8/2007 | Palmer |
| 2007/0185584 A1 | 8/2007 | Kaufmann |
| 2007/0198095 A1 | 8/2007 | VanDer Meulen et al. |
| 2007/0225820 A1 | 9/2007 | Thomas |
| 2007/0244563 A1 | 10/2007 | Roche et al. |
| 2008/0027558 A1 | 1/2008 | Palmer et al. |
| 2008/0051909 A1 | 2/2008 | Wolfe |
| 2009/0149961 A1 | 6/2009 | Dallmann |
| 2009/0164021 A1 | 6/2009 | Dallmann |
| 2009/0198244 A1 | 8/2009 | Leibel |
| 2009/0240336 A1 * | 9/2009 | Vander Meulen et al. . 623/18.11 |
| 2009/0254189 A1 | 10/2009 | Scheker |
| 2010/0010636 A1 | 1/2010 | Shultz et al. |
| 2010/0076568 A1 | 3/2010 | Gupta et al. |
| 2010/0185295 A1 | 7/2010 | Emmanuel |
| 2010/0217331 A1 | 8/2010 | Spagnoli et al. |
| 2010/0222886 A1 | 9/2010 | Wiley et al. |
| 2011/0066250 A1 | 3/2011 | Palmer |
| 2012/0136453 A1 | 5/2012 | Scheker et al. |
| 2012/0150308 A1 | 6/2012 | Gupta et al. |

(56) References Cited

U.S. PATENT DOCUMENTS

| | | |
|---|---|---|
| 2012/0259418 A1 | 10/2012 | Cooney et al. |
| 2012/0277880 A1 | 11/2012 | Winslow et al. |

FOREIGN PATENT DOCUMENTS

| | | |
|---|---|---|
| DE | 10237016 A1 | 2/2004 |
| EP | 0034192 A1 | 8/1981 |
| EP | 0607749 A1 | 7/1994 |
| EP | 1062924 A1 | 12/2000 |
| EP | 1066807 A1 | 1/2001 |
| EP | 1437104 A1 | 7/2004 |
| FR | 2669214 | 5/1992 |
| FR | 2673100 A1 | 8/1992 |
| FR | 2728783 A1 | 7/1996 |
| FR | 2805151 A1 | 8/2001 |
| FR | 2833480 A1 | 6/2003 |
| FR | 2875127 A1 | 3/2006 |
| GB | 1412376 | 11/1975 |
| GB | 2269752 A | 2/1994 |
| GB | 2308068 A | 6/1997 |
| GB | 2392097 A | 2/2004 |
| JP | 7-241306 | 9/1995 |
| JP | 11-332893 | 12/1999 |
| JP | 4170948 B2 | 10/2008 |
| WO | 97/10780 A1 | 3/1997 |
| WO | 2004/026169 A2 | 4/2004 |
| WO | 2006/136940 A2 | 12/2006 |
| WO | 2012154420 A1 | 11/2012 |

OTHER PUBLICATIONS

Hatano et al., "A ceramic prosthesis for the treatment of tumors of the distal radius," The Journal of Bone and Joint Surgery (Br), Dec. 2006, vol. 88-B, No. 12, pp. 1656-1659.

Lawler et al., "Total Wrist Arthroplasty," Bulletin of the NYU Hospital for Joint Diseases, 2006, vol. 64, Nos. 3 and 4, pp. 98-105.

Takwale et al., "Biaxial total wrist replacement in patients with rheumatoid arthritis," The Journal of Bone and Joint Surgery (Br), Jul. 2002, vol. 84-B, No. 5, pp. 692-699.

Tolbert et al., "The Kinetics of Normal and Prosthetic Wrists," J. Biomechanics, 1985, vol. 18, No. 12, pp. 887-897.

Youm et al., "Design of a Total Wrist Prosthesis," Annals of Biomedical Engineering, 1984, vol. 12, p. 247-262.

Swanson et al., "Flexible Implant Arthroplasty of the Radiocarpal Joint," Clinical Orthpedics and Related Research, Jul./Aug. 1984, No. 187, pp. 94-106.

Beckenbaugh, "Implant arthroplasty in the rheumatoid hand and wrist: Current state of the art in the United States," The Journal of Hand Surgery, Sep. 1983, vol. 8, No. 5, Part 2, pp. 675-678.

Levadoux et al., "Total Wrist Arthroplasty with Destot Prostheses in Patients with Posttraumatic Arthritis," The Journal of Hand Surgery, May 2003, vol. 28A, No. 3, pp. 405-413.

Boyer et al., "Distal Radius Hemiathroplasty Combined with Proximal Row Carpectomy: Case Report," The Iowa Orthopaedic Journal, 2010, vol. 30, pp. 168-173.

Gokaraju et al., "Use of a Distal Radius Endoprosthesis Following Resection of a Bone Tumour: A Case Report," Sarcoma, 2009, vol. 2009, Article ID 938295.

U.S. Appl. No. 60/411,824, filed Sep. 18, 2002

International Search Report dated Aug. 31, 2012 for PCT/US2012/037248.

Supplemental European Search Report dated Sep. 23, 2014 for EP 12781791.

Small Bones Innovations, Inc., Remotion Total Wrist System with Precise Guidance Technology, 2007.

Knight et al., "Primary Replacement of the Fractured Radial Head With a Metal Prosthesis", The Journal of Bone and Joint Surgery, 75-B:572-6 (1993).

Sagerman et al., "Silicone Rubber Distal Ulnar Replacement Arthroplasty", Journal of Hand Surgery, 17B:689-693 (1992).

van Schoonhoven et al., "Salvage of Failed Resection Arthroplasties of the Distal Radioulnar Joint Using a New Ulnar Head Prosthesis", The Journal of Hand Surgery, 25A:438-446 (2000).

J. C. Cherry, "Use of Acrylic Prosthesis in the Treatment of Fracture of the Head of the Radius", The Journal of Bone and Joint Surgery, 35B:70-71 (1953).

Stanley et al., "The Swanson Ulnar Head Prosthesis for Post-Traumatic Disorders of the Distal Radio-Ulnar Joint", Journal of Hand Surgery, 17B:682-688 (1992).

Hand Innovations LLC, Surgical Solutions for the Upper Extremity, Herbert Ulnar Head Prosthesis Hand Surgery, date not known.

Extended European Search Report for Application No. 12781791.4 dated Sep. 23, 2014.

* cited by examiner

WRIST IMPLANT FOR CARPAL HEMIARTHROPLASTY

CROSS-REFERENCE TO RELATED APPLICATIONS

This application is a U.S. national stage of International Application No. PCT/US2012/037248, filed May 10, 2012, which claims the benefit of U.S. Provisional Patent Application No. 61/485,447, filed May 12, 2011, each of which is incorporated herein by reference in its entirety.

FIELD OF THE INVENTION

The present invention, in some embodiments, relates to prosthetic orthopedic implants. Some embodiments of the invention relate to a prosthetic wrist implant. More particularly, in some embodiments, the invention relates to a wrist implant for carpal hemiarthroplasty.

SUMMARY OF THE INVENTION

In some embodiments, the present invention relates to a wrist implant for carpal hemiarthroplasty including an articular component having a generally convex articular surface shaped to conform to an unresected distal end of a radius bone, a bearing component rigidly fixed to the articular component opposite the convex articular surface and having a bearing surface, and a carpal plate rotatably coupleable to the bearing component having a proximal surface and a distal surface, the proximal surface having a contour substantially conforming to the bearing surface.

In some embodiments, the convex articular surface includes a first curvature in a first direction defined by a major radius of curvature and a second curvature in a second direction perpendicular to the first direction defined by a minor radius of curvature, the major radius of curvature being larger than the minor radius of curvature. In some embodiments, the convex articular surface is shaped to substantially conform to the lunate and scaphoid fossae of the unresected distal end of a radius bone. In further embodiments, the bearing surface has a concave curvature defined by a radius of curvature larger than the major radius of curvature of the convex articular surface. In some embodiments, the articular component is configured to articulate with the unresected distal end of a radius bone about two perpendicular axes of rotation. In certain preferred embodiments, the implant is configured to articulate with the distal end of the radius in at least one of radial deviation, ulnar deviation, extension, and flexion. In some embodiments, no component of the implant is configured to be fixed to or inserted into the radius bone and/or an ulna bone when implanted.

The articular component, according to some embodiments, defines a concavity opposite the convex articular surface and includes a lip surrounding the concavity. In some variations of these embodiments, the proximal portion of the bearing component is received in the concavity, and the bearing component further includes a flange abutting the lip. In some embodiments, the proximal portion of the bearing component includes a dimension equal to a dimension of the concavity. In some embodiments, the articular component includes a ridge extending into the concavity and the bearing component includes a groove for receiving the ridge.

The articular component in some embodiments may be made of a metal or metal alloy. For example, in some embodiments, the articular component is made of a cobalt-chrome alloy. The bearing component is made from a polymer according to some preferred embodiments. In some embodiments, the bearing component is made from ultra high molecular weight polyethylene.

In some embodiments, the bearing surface has a concave curvature and the proximal surface of the carpal plate has a convex curvature. In some embodiments, the concave curvature of the bearing surface and the convex curvature of the proximal surface are defined by substantially the same radius of curvature. The carpal plate in some embodiments further includes a protrusion extending from the proximal surface. In some embodiments, bearing component is configured to rotate with respect to the carpal plate about the protrusion. The protrusion in some embodiments includes a spheroidal portion and a support securing the spheroidal portion to the proximal surface of the carpal plate. In some variations of these embodiments, the spheroidal portion includes a diameter larger than a diameter of the support. In further variations of these embodiments, the bearing component includes a socket opening to the bearing surface for receiving the protrusion therein.

The implant according to embodiments of the present invention may also include a first carpal screw and a second carpal screw, each screw having a head and a shaft that is at least partially threaded. In some embodiments, bearing component includes a first cavity for receiving the head of the first carpal screw and a second cavity for receiving the head of the second carpal screw. In certain preferred embodiments, the first carpal screws and the second carpal screw are engageable with the bearing component to limit the rotational articulation between the bearing component and the carpal component. In some embodiments, the first carpal screw is longer than the second carpal screw. In some embodiments, the first carpal screw and the second carpal screw have the same length.

An implant according to certain embodiments of the invention may be used to treat one or more of the following conditions: 1) non-inflammatory degenerative joint disease including osteoarthritis, traumatic arthritis, Kienbock's disease and other avascular necrosis (AVN); 2) rheumatoid arthritis; 3) revision where other wrist implants or treatments have failed; 4) scapholunate advanced collapse (SLAC) and other functional deformities; and 5) trauma including fractures of the carpal bones.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention can be embodied in different forms and thus should not be construed as being limited to the embodiments set forth herein.

DETAILED DESCRIPTION

The present subject matter will now be described more fully hereinafter with reference to the accompanying Figures and Examples, in which representative embodiments are shown. The present subject matter can, however, be embodied in different forms and should not be construed as limited to the embodiments set forth herein. Rather, these embodiments are provided to describe and enable one of skill in the art. All publications, patent applications, patents, and other references mentioned herein are incorporated by reference in their entirety.

Referring to the drawings in detail, wherein like reference numerals indicate like elements throughout, there is shown in FIGS. 1A-5 a wrist implant, generally designated 100, in accordance with an exemplary embodiment of the present invention. In certain embodiments, wrist implant 100 is configured for implantation into the wrist of a patient to replace damaged or degenerated wrist structure. In some embodiments, wrist implant 100 is configured as a carpal hemiarthroplasty implant. In preferred embodiments, wrist implant 100 is configured as a carpal hemiarthroplasty implant to replace bones of the proximal carpal row, particularly the scaphoid and lunate bones. According to some embodiments, no component of wrist implant 100 is intended to be fixed to or inserted into the radius bone and/or ulna bone. For example, wrist implant 100 when used for carpal hemiarthroplasty in accordance with certain embodiments does not require an intramedullary stem or other component inserted into to the distal radius or ulna. Moreover, wrist implant 100 is preferably sized and configured for implantation without requiring removal of the distal carpal bones or resection of normal bone tissue of the distal radius or ulna.

Figure 1A:
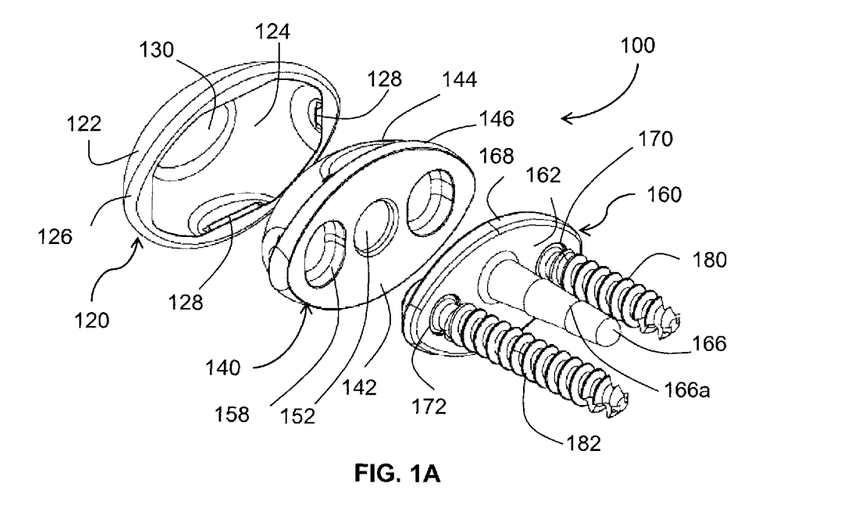
FIGS. 1A and 1B show exploded perspective views of a wrist implant in accordance with an exemplary embodiment of the present invention.
Figure 1B:
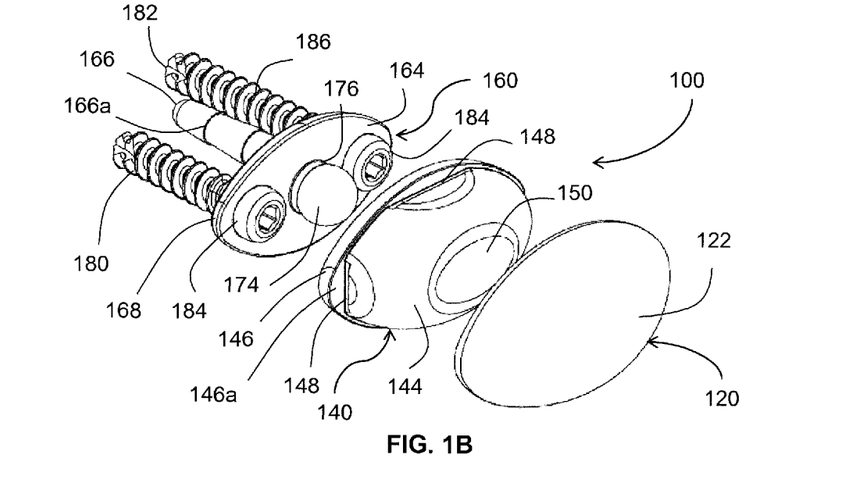
Figure 5:
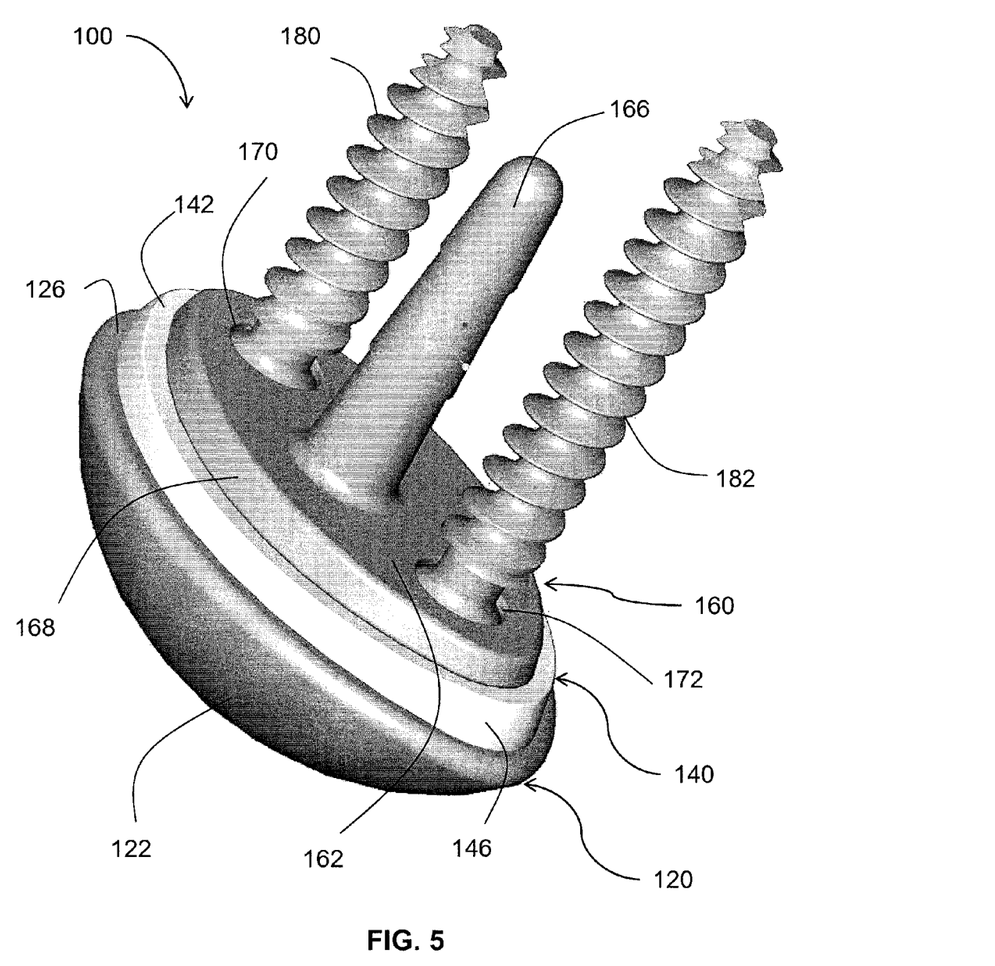
FIG. 5 shows a perspective view of a wrist implant in accordance with an exemplary embodiment of the present invention.

Referring to FIGS. 1A, 1B, and 5, wrist implant 100 generally includes articular component 120, carpal plate 160, and bearing component 140. In some embodiments, wrist implant 100 further includes one or more, preferably two, carpal screws 180 and 182.

Figure 2A:
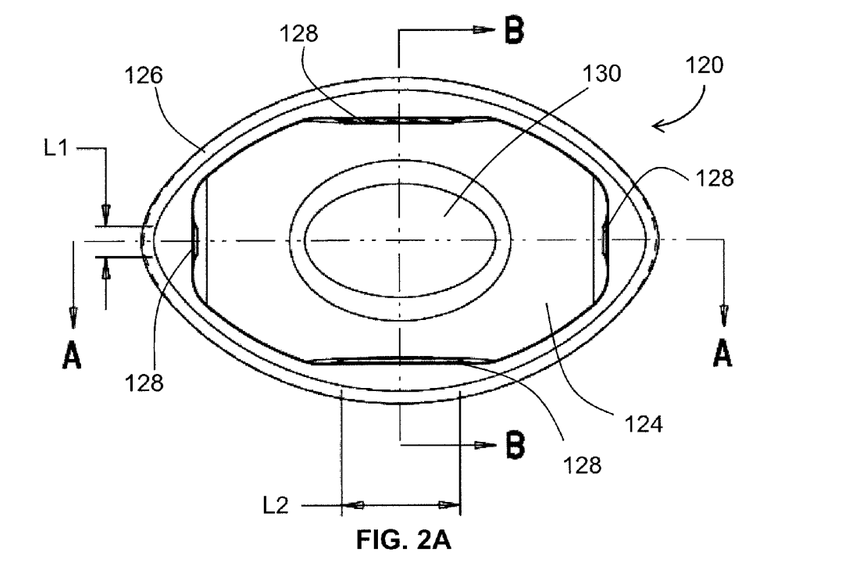
FIG. 2A shows an end view of an articular component in accordance with an exemplary embodiment of the present invention.
Figure 2B:
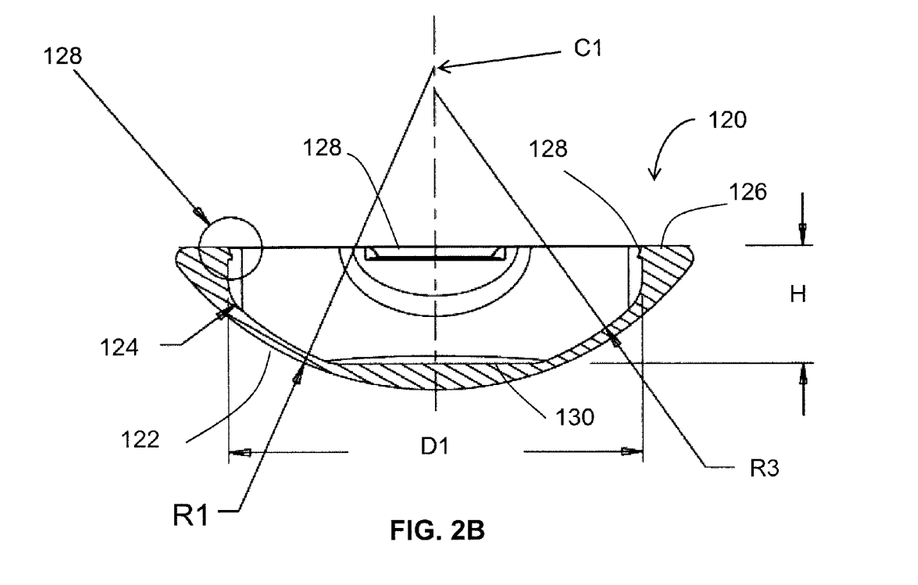
FIGS. 2B and 2C respectively show cross-sectional views of the articular component taken across lines A-A and B-B of FIG. 2A.

Articular component 120 in certain embodiments is configured to directly contact and articulate with the distal end of a radius bone in at least one of radial deviation, ulnar deviation, extension, and flexion. In some embodiments, articular component 120 is configured to articulate with the distal end of the radius bone about at least two perpendicular axes of rotation. For example, in some embodiments, a first axis of rotation extends in the dorsal-palmar direction corresponding to radial and ulnar deviation and a second axis of rotation extends in the radial-ulnar direction corresponding to extension and flexion. Referring to FIG. 2B, in one embodiment a first axis of rotation relative to articular component 120 extends perpendicular to the plane of the page at point C1.

Figure 2C:
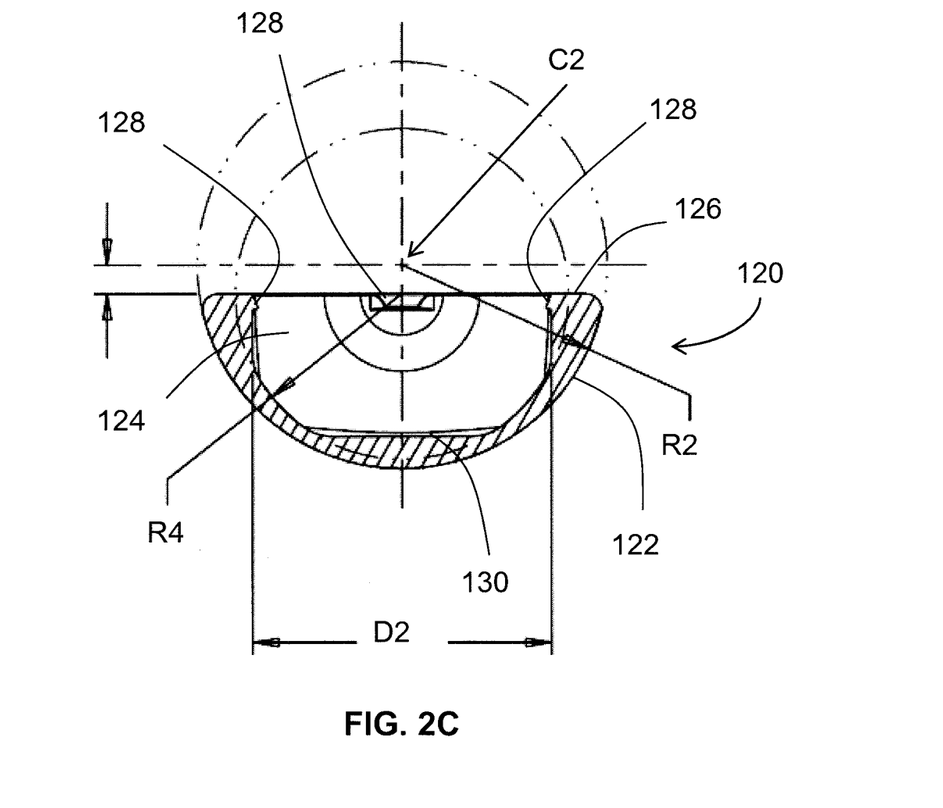

Referring to FIG. 2C, in one embodiment a second axis of rotation relative to articular component 120 extends perpendicular to the plane of the page at point C2.

With particular reference to FIGS. 1A-2C, in some embodiments articular component 120 includes proximal articular surface 122. In some embodiments, articular component 120 further defines cavity 124 opposite proximal articular surface 122. In some embodiments, proximal articular surface 122 is configured to seat against the distal end of a radius bone. In some embodiments, proximal articular surface 122 is shaped to generally conform to an unresected distal end of a radius bone. In certain embodiments, proximal articular surface 122 includes a continuous convex contour and is shaped to substantially conform to the lunate and scaphoid fossae of an unresected distal end of a radius bone. Proximal articular surface 122 in some embodiments includes a first curvature in a first direction defined by a major radius of curvature R1 (FIG. 2B) and a second curvature in a second direction perpendicular to the first direction defined by a minor radius of curvature R2 (FIG. 2C). Minor radius of curvature R2, in preferred embodiments, is smaller than major radius of curvature R1. In some embodiments, the first direction generally corresponds to the ulnar-radial direction and the second direction corresponds to the dorsal-palmar direction when implanted in the wrist. In some embodiments, the first curvature is selected to emulate the curve traced by the proximal portion of the scaphoid-lunate complex during normal articulation of the human wrist in radial and ulnar deviation. In some embodiments, the second curvature is selected to emulate the curve traced by the proximal portion of the scaphoid-lunate complex during normal articulation of the human wrist in flexion and extension.

In some embodiments articular component 120 defines a cavity 124 having a depth H opposite proximal articular surface 122, as shown in FIG. 2B. Cavity 124, in some embodiments, is configured to receive at least a portion of bearing component 140 and may include one or more securements 128 for attachment thereto, as will be described further below. Referring to FIGS. 2B and 2C, the inner surface of articular component 120 which defines cavity 124 may in some embodiments have a curvature in the first direction defined by a major radius of curvature R3 and in the second direction defined by a minor radius of curvature R4 smaller than R1 and R2 respectively. Moreover, in some embodiments, cavity 124 has a major dimension D1 in the first direction and a minor dimension D2 that is smaller than D1 in the second direction. In some embodiments, articular component 120 includes one or more flattened surfaces 130 on the interior of cavity 124. In some embodiments, articular component 120 further includes lip 126 that surrounds the opening of cavity 124.

Articular component 120 may be made from any suitable biocompatible material known in the art. In some embodiments, articular component 120 is made from a rigid nonresorbable material. In preferred embodiments, articular component 120 is made from a biocompatible metallic material. Exemplary materials for the articular component 120 include titanium, titanium alloys, cobalt alloys, cobalt-chrome (Co—Cr) alloys, cobalt-chrome-molybdenum (Co—Cr—Mo) alloys, stainless steel, and combinations thereof. In other embodiments, articular component 120 or a portion thereof is made from pyrolytic carbon. In another embodiment, articular component 120 or a portion thereof is made from a biocompatible ceramic material. In some embodiments, articular component 120 is machined from a single, monolithic piece of material. In some embodiments, for example, articular component 120 can be made through conventional machining from wrought barstock. In some embodiments, articular component 120 can be formed using electrical discharge machining (EDM). In some embodiments, articular component 120 can be molded, cast, and/or ground. In some embodiments, articular component 120 may be constructed as separate components that are later assembled together. In some of these embodiments, the separate components may be made from the same or different materials.

In certain preferred embodiments, any surface of articular component 120 that is configured to contact bone is mirror polished. In some embodiments, at least proximal articular surface 122 is mirror polished. In some embodiments, mirror polishing helps to reduce friction and wear between proximal articular surface 122 and the distal surface of the radius bone during articulation. In some embodiments, lip 126 is also mirror polished. In some embodiments, the surfaces defining cavity 124 are not mirror polished. In some embodiments, articular surface 122 may be provided with a coating configured to reduce wear. In some embodiments, articular surface 122 is coated with titanium nitride. In some embodiments, articular surface 122 is treated with ion bombardment.

Referring again to FIGS. 1A, 1B, and 5, wrist implant 100, according to certain embodiments of the present invention, may further include carpal plate 160. In some embodiments, carpal plate 160 is configured to contact and be secured to at least one distal carpal bone of the wrist. In some embodiments, carpal plate 160 may have the configuration of the carpal plates described in U.S. Pat. Nos. 7,625,408, 7,628,819, and U.S. Patent Application Publication No. 2010-0076568, which are each incorporated herein by reference in their entireties. Carpal plate 160, in preferred embodiments, generally includes distal surface 162, proximal surface 164 opposite distal surface 162, periphery 168, and carpal stem 166. In some embodiments, carpal plate 160 further defines one or more screw holes 170 and 172 for receiving carpal screws 180 and 182.

In some embodiments, carpal plate 160 may have a planoconvex configuration. In some embodiments, distal surface 162 is substantially flat. In some embodiments, proximal surface 164 is convexly curved. In some embodiments, proximal surface 164 is convexly curved along a spherical radius of curvature. In some embodiments, the radius of curvature of proximal surface 164 is larger than either the major radius of curvature R1 or the minor radius of curvature R2 of articular surface 122.

According to some embodiments, carpal stem 166 extends distally from distal surface 162 and is configured for insertion into a distal carpal bone (e.g., capitate). In some embodiments, carpal stem 166 extends perpendicularly from distal surface 162. As shown in the illustrated embodiments, carpal stem 166 may be tapered and may include retaining ridges 166a to assist in securing carpal stem 166 to the distal carpal bone. In other embodiments, carpal stem 166 may have a constant diameter substantially throughout its length. In preferred embodiments, carpal stem 166 has a length such that, when implanted, carpal stem 166 does not extend into or beyond the carpal-metacarpal joint of the wrist. In some embodiments, carpal stem 166 may extend from a location offset from the center of distal surface 162.

Referring to FIG. 1A, in some embodiments, carpal plate 160 includes one or more, preferably two, screw holes 170 and 172 that extend through the entire thickness of carpal plate 160 from distal surface 162 to proximal surface 164. Screw holes 170 and 172, in some embodiments, may be spherically countersunk on the proximal surface 164. In some embodiments, screw holes 170 and 172 have the same diameter. In some embodiments, screw holes 170 and 172 are substantially aligned with a central longitudinal axis of carpal plate 160 (e.g., extending in the radial-ulnar direction when implanted). In some embodiments, carpal stem 166 is positioned on distal surface 162 at a location offset dorsally from alignment with screw holes 170 and 172. In some embodiments, the dorsal offset of carpal stem 166 is configured to accommodate the natural arch of the carpal bones.

Referring to FIG. 1B, in some embodiments carpal plate 160 further includes a protrusion 174 extending proximally from proximal surface 164. In some embodiments, protrusion 174 extends from proximal surface 164 along a central axis perpendicular to proximal surface 164. In some embodiments, protrusion 174 is secured to proximal surface 164 by support 176. Protrusion 174, in some embodiments, has a width larger than the width of support 176. In some embodiments, protrusion 174 is spheroidal in shape with a diameter larger than the diameter of support 176. In some embodiments, protrusion 174 generally extends from the center of proximal surface 164. In some embodiments, protrusion 174 is positioned on proximal surface 164 at a location centrally positioned between and aligned with screw holes 170 and 172. In preferred embodiments, protrusion 174 is positioned such that when implanted into a patient, protrusion 174 extends from proximal surface 164 in a direction substantially aligned with or parallel to the long axis of the third metacarpal bone of the patient (e.g., 312 of FIG. 6).

Carpal plate 160 may be made from any suitable biocompatible material known in the art. In some embodiments, carpal plate 160 is made from a rigid nonresorbable material. In some embodiments, carpal plate 160 is made from the same material as articular component 120. In preferred embodiments, carpal plate 160 is made from a biocompatible metallic material. Exemplary materials for carpal plate 160 include titanium, titanium alloys, cobalt alloys, cobalt-chrome (Co—Cr) alloys, cobalt-chrome-molybdenum (Co—Cr—Mo) alloys, stainless steel, and combinations thereof. In some embodiments, the components of carpal plate 160, including carpal stem 166, protrusion 174, and support 176, are integrally formed from a single, monolithic piece of material. In some embodiments, carpal plate 160 is machined from a single piece of material. In some embodiments, for example, carpal plate 160 can be made through conventional machining from wrought barstock. In some embodiments, carpal plate 160 can be formed using electrical discharge machining (EDM). In some embodiments, carpal plate 160 can be molded, cast, and/or ground. In some embodiments, carpal plate 160 may be constructed as separate components that are later assembled together. In some of these embodiments, the separate components may be made from the same or different materials. For example, in one embodiment, carpal stem 166 may be constructed as a separate component from and later joined to distal surface 162. In this embodiment, carpal stem 166 may be constructed from a material different than other components of carpal plate 160.

In some embodiments, at least a portion of carpal plate 160 is mirror polished. In some embodiments, only a portion of carpal plate 160 is mirror polished. In preferred embodiments, proximal surface 164 is mirror polished. In some embodiments, protrusion 174 and support 176 are mirror polished. In some embodiments, periphery 168 is mirror polished. In some embodiments, distal surface 162 and/or carpal stem 166 are not mirror polished. In some embodiments, proximal surface 164 may be provided with a coating configured to reduce wear. In some embodiments, proximal surface 164 is coated with titanium nitride. In some embodiments, proximal surface 164 is treated with ion bombardment.

In some embodiments, distal surface 162 and/or carpal stem 166 may be coated with a suitable material to promote osseointegration and bone ingrowth. In some embodiments, distal surface 162 and/or carpal stem 166 is coated with titanium plasma coating. In some embodiments, distal surface 162 and/or carpal stem 166 is coated with hydroxyapatite. In some embodiments, distal surface 162 and/or carpal stem 166 is sintered bead coated. In some embodiments, distal surface 162 and/or carpal stem 166 is coated with porous tantalum (e.g., TRABECULAR METAL™).

According to some embodiments of the present invention, wrist implant 100 may also include carpal screws 180 and 182 configured for insertion into bones of the distal carpus. Carpal screws 180 and 182 may have the same configuration as the screws described in U.S. Pat. Nos. 7,625,408, 7,628,819, and U.S. Patent Application Publication No. 2010-0076568, which are each incorporated herein by reference in their entireties. Referring to FIGS. 1A and 1B, in some embodiments carpal screws 180 and 182 include a head 184 and shaft 186. Carpal screws 180 and 182 may, in some embodiments, be self-tapping screws. In some embodiments, shaft 186 is at least partially threaded. In some embodiments, shaft 186 may be provided with threads particularly configured for securement to cancellous bone. In some embodiments, carpal screws 180 and 182 may be of the same length. In other embodiments, carpal screw 182 may be longer than carpal screw 180.

In preferred embodiments, head 184 of carpal screws 180 and 182 may have a spherical curvature and have a diameter that is larger than the diameter of screw holes 170 and 172. In some embodiments, the spherical curvature of head 184 allows for angular adjustment of carpal screws 180 and 182 relative to carpal plate 160 when received through screw holes 170 and 172.

Figure 4A:
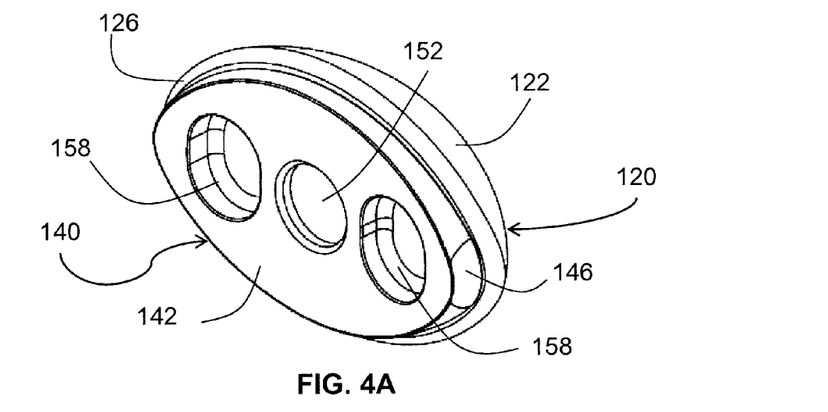
FIG. 4A shows a perspective view of an articular component assembled with a bearing component in accordance with an embodiment of the present invention.
Figure 4B:
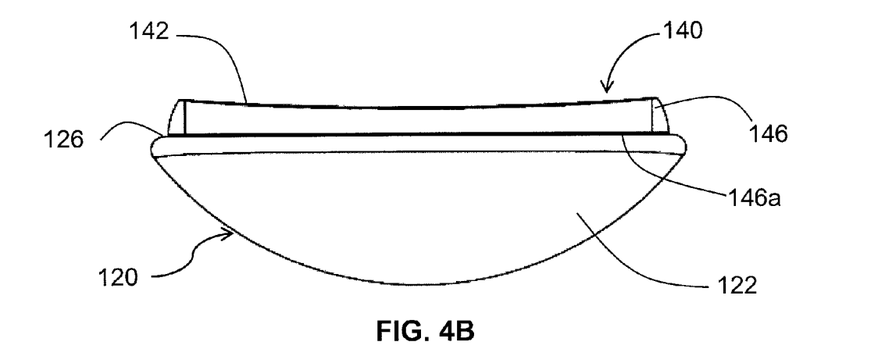
FIGS. 4B and 4C respectively show a plan view and an elevational view of the assembly shown in FIG. 4A.
Figure 4C:
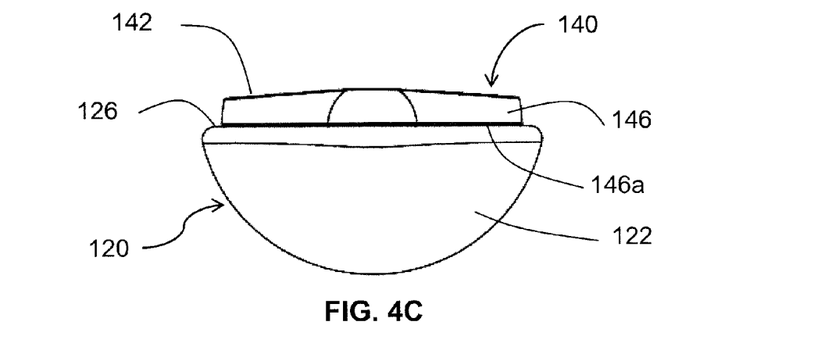
Figure 4D:
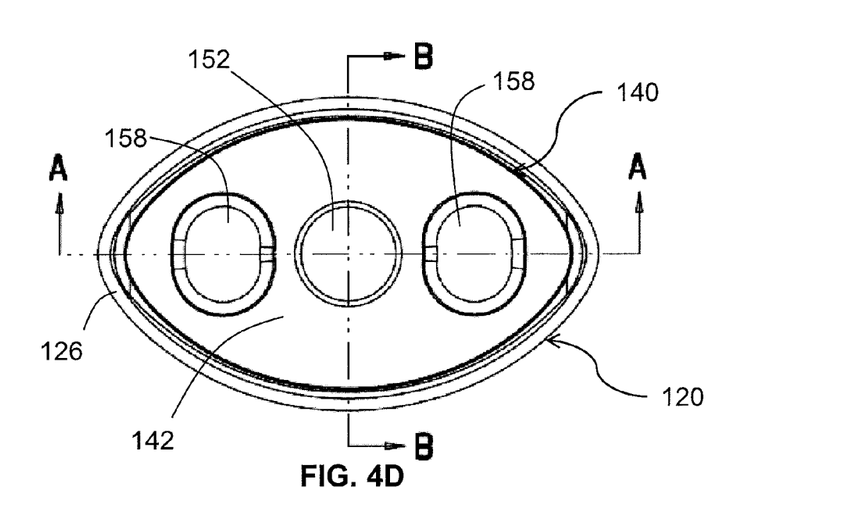
FIG. 4D shows an end view of the assembly shown in FIG. 4A.

As shown in FIGS. 1A, 1B, and 5, in some embodiments of the present invention, wrist implant 100 further includes bearing component 140. In some embodiments, bearing component 140 is configured to be positioned between articular component 120 and carpal plate 160. In some embodiments, bearing component 140 is configured to secure articular component 120 with carpal plate 160. In some embodiments, bearing component 140 is configured to be rigidly fixed to articular component 120 such that there is substantially no movement of articular component 120 relative to bearing component 140 when articular component 120 is engaged with bearing component 140. In some embodiments, articular component 120 is configured as a cap or shell to fit over bearing component 140, for example, as shown in FIGS. 4A-5. In some embodiments, articular component 120 covers the majority of the surface area of bearing component 140.

In some embodiments, bearing component 140 is configured to articulate with carpal plate 160 when engaged therewith. In some embodiments, carpal plate 160 is configured to rotate with respect to bearing component 140. In some embodiments, carpal plate 160 is configured to rotate with respect to bearing component 140 about an axis of rotation generally perpendicular to distal surface 162.

In some embodiments, bearing component 140 includes a distal bearing surface 142 for abutment with proximal surface 164 of carpal plate 160. In preferred embodiments, distal bearing surface 142 has a concave curvature conforming to the convex curvature of proximal surface 164 of carpal plate 160. In some embodiments, distal bearing surface 142 is concavely curved and proximal surface 164 is convexly curved with substantially the same radius of curvature, which is preferably larger than either R1 or R2.

Referring to FIGS. 1A and 4D-4F, in some embodiments bearing component 140 includes a socket 152 which opens to distal bearing surface 142. In some embodiments, socket 152 opens at the center of distal bearing surface 142. In preferred embodiments, socket 152 is sized and configured to receive protrusion 174 of carpal plate 160 when bearing component 140 is engaged with carpal plate 160. In some embodiments, bearing component 140 is configured to rotate with respect to carpal plate 160 about protrusion 174 when protrusion 174 is received in socket 152.

Figure 4E:
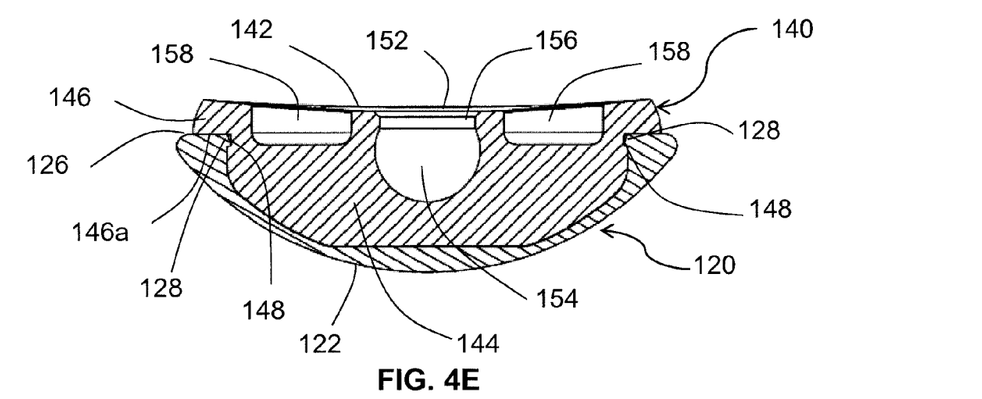
FIGS. 4E and 4F respectively show cross-sectional views of the assembly taken across lines A-A and B-B of FIG. 4D.
Figure 4F:
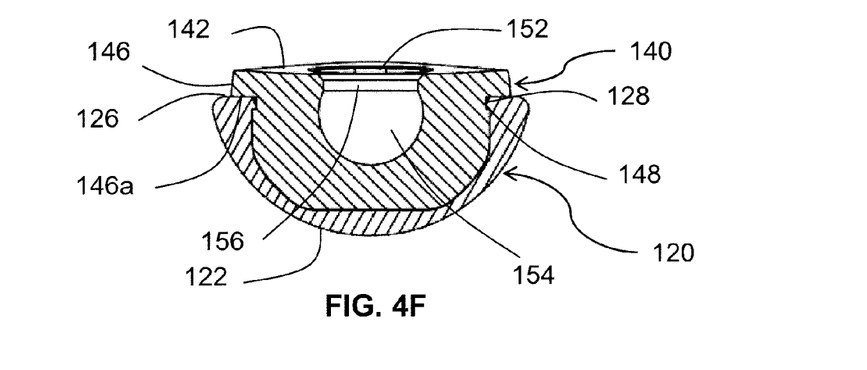

Referring to FIGS. 4E and 4F, in some embodiments socket 152 may include a spheroidal portion 154 and a narrowed rim 156. In some embodiments, spheroidal portion 154 has a diameter greater than the diameter of protrusion 174, and rim 156 has a diameter less than the diameter of protrusion 174. In some embodiments, rim 156 is configured to retain protrusion 174 in spheroidal portion 154 when protrusion 174 is received in socket 152. In some embodiments, socket 152 engages with protrusion 174 via an interference fit.

In some embodiments, bearing component 140 includes one or more, preferably two, cavities 158 which open to distal bearing surface 142. The cavities 158, in preferred embodiments, are sized and configured to receive heads 184 of screws 180 and 182. Cavities 158, in some embodiments, are of an oval, ellipsoidal, arcuate or racetrack shape. In general, cavities 158 are shaped to allow a degree of movement of heads 184 within cavities 158 so as to allow for rotational articulation between bearing component 140 and carpal plate 160 according to some embodiments.

Figure 3A:
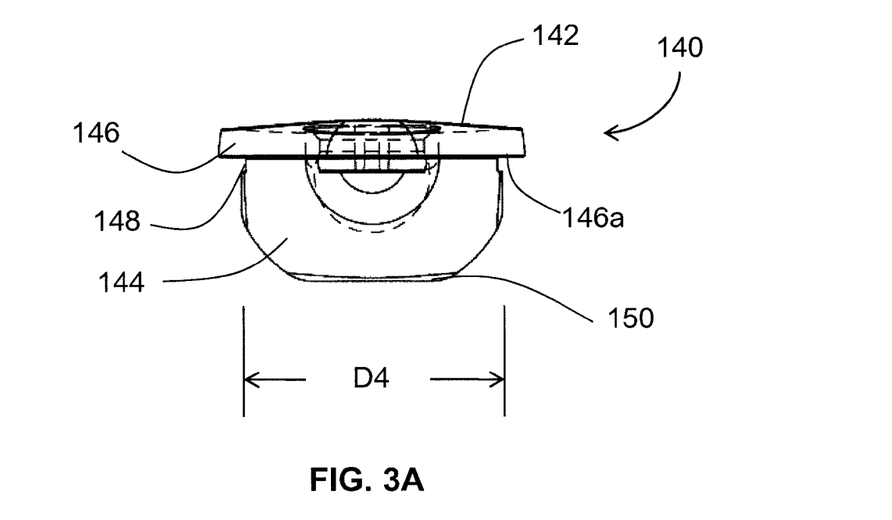
FIG. 3A and 3B respectively show an elevational view and a plan view of a bearing component in accordance with an exemplary embodiment of the present invention.
Figure 3B:
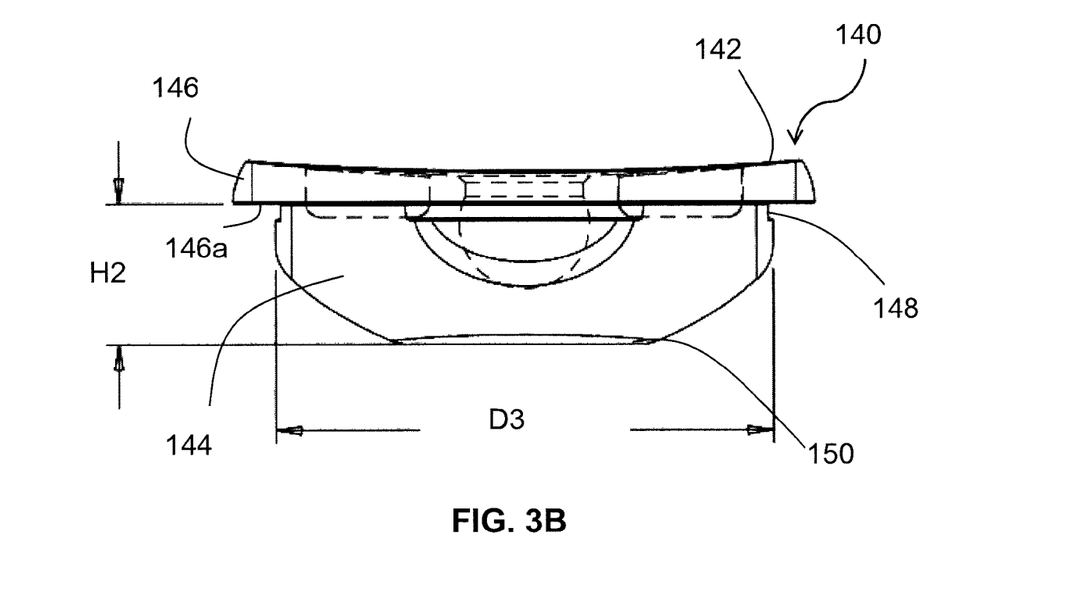

In some embodiments, bearing component 140 further includes a proximal portion 144 opposite distal bearing surface 142. In some embodiments, proximal portion 144 is configured to engage with articular component 120. In some embodiments, proximal portion 144 is configured to be rigidly fixed to articular component 120 such that there is substantially no movement of articular component 120 relative to bearing component 140 when articular component 120 is engaged with proximal portion 144. In some embodiments, proximal portion 144 is sized and shaped to be received in cavity 124 of articular component 120. As shown in FIGS. 4E and 4F, in some embodiments, articular component 120 covers the majority of the surface area of bearing component 140 proximal to bearing surface 142. In some embodiments, articular component 120 completely surrounds proximal portion 144. In some embodiments, proximal portion 144 is shaped to conform to the inner surfaces of cavity 124. In some embodiments, proximal portion 144 includes a convex curvature which may be shaped to match the curvature of cavity 124. Referring to FIGS. 3A and 3B, in some embodiments proximal portion 144 has first and second dimensions D3 and D4 substantially equal to major and minor dimensions D1 and D2 of cavity 124. In some embodiments, proximal portion 144 further has a height H2 substantially equal to depth H of cavity 124. In some embodiments, proximal portion 144 includes one or more flattened surfaces 150 shaped to substantially match flattened surfaces 130 of articular component 120. In some embodiments, socket 152 extends from distal bearing surface 142 into proximal portion 144. In some embodiments, cavities 158 extend from distal bearing surface 142 into proximal portion 144.

Bearing component 140 may be secured to articular component 120 by any suitable means known in the art. As mentioned above, in some embodiments articular component 120 includes securements 128 for attachment to bearing component 140. In some embodiments, securements 128 may be positioned at or near the opening of cavity 124. As shown in the FIG. 2A, in some embodiments securements 128 include discontinuous retaining ridges or tabs extending from one or more inner surfaces of cavity 124. In some embodiments, the retaining ridges or tabs may have different lengths L1 and L2.

According to some of these embodiments, proximal portion 144 may include one or more grooves 148 configured to receive the ridges or tabs to form a locking engagement therewith when bearing component 140 is engaged with articular component 120 (see FIGS. 4E and 4F). Grooves 148, in some embodiments, are arranged around a periphery of proximal portion 144. In some alternative embodiments, the position of the grooves and ridges or tabs may be reversed such that proximal portion 144 includes the ridges or tabs and cavity 124 includes the grooves for receiving the ridges or tabs. While articular component 120 of the illustrated embodiments is shown having four ridges, it should be understood that any suitable number of ridges may be included in other embodiments.

In some embodiments, proximal portion 144 is configured to be snap fit into cavity 124 to secure bearing component 140 to articular component 120. In some embodiments, an adhesive or cement may be applied between bearing component 140 and articular component 120. In some embodiments, bearing component 140 and articular component 120 are secured together by an interference or press fit. In some embodiments, bearing component 140 and articular component 120 are secured by pinning. In some embodiments, bearing component 140 and articular component 120 are welded, soldered, fused together. In some embodiments, bearing component 140 is directly molded into cavity 124 of articular component 120.

Referring to FIGS. 4E and 4F, in some embodiments, the periphery of distal bearing surface 142 extends beyond proximal portion 144 forming a flange 146. In some embodiments grooves 148 are defined in part by proximal surface 146a of flange 146. In some embodiments, proximal surface 146a of flange 146 is configured to abut lip 126 of articular component 120 when articular component 120 is secured to bearing component 140. In certain embodiments, flange 146 is configured to form a seal with lip 126 so as to close cavity 124 of articular component 120. In some embodiments, lip 126 extends beyond flange 146. As shown for example in FIGS. 4A-4F, in some embodiments articular component 120 completely surrounds all portions of bearing component 140 proximal to proximal surface 146a of flange 146.

In some embodiments, bearing component 140 is made from a material different than the material used to construct articular component 120 or carpal plate 160. In some embodiments, bearing component 140 is made from a material selected to have a low coefficient of friction with proximal surface 164 of carpal plate 160. In some embodiments, bearing component 140 is made from a biocompatible polymer material. In some embodiments, bearing component 140 is made from a self-lubricating material. In preferred embodiments, bearing component 140 is made from ultra high molecular weight polyethylene (UHMWPE). In other embodiments, bearing component is made from polyether ether ketone (PEEK). In some embodiments, bearing component 140 may be machined from a single piece of material, molded, cast, or formed by other techniques known in the art.

In certain embodiments, wrist implant 100 is implanted into the wrist of a patient to replace damaged or degenerated wrist structure. In preferred embodiments, wrist implant 100 is used as a carpal hemiarthroplasty implant to replace bones of the proximal carpal row, particularly the scaphoid and lunate bones. In this procedure, according to certain embodiments, no component of wrist implant 100 is intended to be fixed to or inserted into the radius bone and/or ulna bone. For example, wrist implant 100 when used for carpal hemiarthroplasty does not require an intramedullary stem or other component inserted into to the distal radius or ulna. Moreover, wrist implant 100 is preferably sized and configured for implantation without requiring removal of the distal carpal bones or resection of normal bone tissue of the distal radius or ulna.

Except for steps relating to the drilling of and insertion of a radial component into the distal radius bone, the implantation methods described in U.S. Pat. Nos. 7,625,408, ,628,819, and U.S. Patent Application Publication No. 2010-0076568 may be used to implant wrist implant 100 according to some embodiments of the invention.

In some embodiments, certain bones of the carpus are resected across the proximal carpal row. The lunate, triquetrum, proximal scaphoid, and the head of the capitate may be resected in some embodiments, though preferably only the lunate and the proximal pole of the scaphoid are removed. Preferably the carpal resection is performed along a plane generally perpendicular to the long axis of the radius bone. In some embodiments, bones of the distal carpal row are not removed. Furthermore, in preferred embodiments, normal bone tissue of the distal radius bone and ulna is not resected. In some embodiments, heterotopic bone or osteophytes may be removed from the scaphoid and lunate fossae of the distal radius if present.

In some embodiments, after the carpal bones are resected, a hole is drilled into the center of the capitate bone to receive carpal stem 166 of carpal plate 160. Preferably, the hole does not penetrate into carpal-metacarpal joint. In some embodiments, additional holes are also drilled in the hamate bone and remaining distal scaphoid portion for receiving carpal screws 180 and 182. After drilling the holes, in some embodiments, carpal plate 160 is positioned into place such that carpal stem 166 is aligned with the hole drilled in the capitate bone and screw holes 170 and 172 are aligned with the holes drilled in the hamate and scaphoid bones. Carpal stem 166 is then inserted into the drilled capitate bone and carpal screws 180 and 182 are positioned through screw holes 170 and 172 and screwed into the hamate and scaphoid bones.

In some embodiments, carpal screws 180 and 182 can be selected to have the same or different lengths. In some embodiments carpal screw 182 is of a length sufficient enough to penetrate into the second metacarpal bone. In other embodiments, carpal screw 182 is selected to have a length that does not penetrate the carpal-metacarpal joint. In some embodiments, carpal screw 180 is selected to have a length that does not penetrate into the carpal-metacarpal joint. In some embodiments, several pairs of carpal screws of varying lengths are provided and the appropriate screws are selected for use as carpal screws 180 and 182 with wrist implant 100 at the time of surgery depending upon patient anatomy and/or need for supplemental fixation (e.g., securement of the carpal screw to a metacarpal bone).

Once carpal plate 160 is secured to the carpal bones, bearing component 140 is engaged with carpal plate 160. In some embodiments, bearing component 140 is engaged with carpal plate 160 by aligning socket 152 with protrusion 174, aligning cavities 158 with heads 184 of carpal screws 180 and 182, and applying sufficient force onto bearing component 140 such that protrusion 174 is pressed into socket 152. In some embodiments, distal bearing surface 142 of bearing component 140 directly abuts proximal surface 164 of carpal plate 160 when bearing component 140 is engaged with carpal plate 160. In some embodiments, engagement of bearing component 140 with carpal plate 160 provides for a degree of rotational motion of the bearing component 140 relative to carpal plate 160 about protrusion 174. In some embodiments, after implantation, engagement of bearing component 140 with carpal plate 160 provides for a degree of rotational motion of the bearing component 140 relative to carpal plate 160 about an axis generally parallel to the long axis of the third metacarpal. In some embodiments, heads 184 of carpal screws 180 and 182 by virtue of being disposed in cavities 158 of bearing component 140 limits the range of rotational motion of bearing component 140 relative to carpal plate 160. In some embodiments, rotational motion of bearing component 140 relative to carpal plate 160 is limited to about five degrees in either rotational direction or about ten degrees total.

In some embodiments, articular component 120 is engaged with bearing component 140 prior to engagement of bearing component 140 with carpal component 160. In other embodiments, articular component 120 is engaged with bearing component 140 after engagement of bearing component with carpal component 160. In some embodiments, engagement of articular component 120 and bearing component 140 includes securing articular component 120 to bearing component 140 as described above (e.g., snap fitting articular component 120 onto proximal portion 144). In preferred embodiments, articular component 120 is rigidly fixed to bearing component 140 so as to substantially prevent any movement of articular component 120 relative to bearing component 140 when articular component 120 is engaged with bearing component 140.

Once implanted, proximal articular surface 122 of articular component 120 directly contacts and articulates with the distal radius according to some embodiments. In some embodiments, the articulation of proximal articular surface 122 with the distal end of the radius bone mimics the natural articulation of the lunate and scaphoid bones of a healthy wrist with the distal end of the radius bone. In preferred embodiments, articular component 120 articulates with the distal end of the radius bone to provide for radial deviation, ulnar deviation, extension, and flexion.

The carpal hemiarthroplasty wrist implants according to certain embodiments of the invention may be particularly useful for the following indications: 1) non-inflammatory degenerative joint disease including osteoarthritis, traumatic arthritis, Kienbock's disease and other avascular necrosis (AVN); 2) rheumatoid arthritis; 3) revision where other wrist implants or treatments have failed; 4) scapholunate advanced collapse (SLAC) and other functional deformities; and 5) trauma including fractures of the carpal bones.

Current treatment options for these indications include proximal row carpectomy (PRC), bone fusion (e.g., wrist fusion or radio-carpal fusion), and total wrist arthroplasty (TWA). In some embodiments, the carpal hemiarthroplasty implants of the present invention offer a more conservative alternative to these treatment options and provide certain advantages, particularly where a patient's native distal radius is intact and not pathologic or symptomatic. For example, wrist implant 100 in certain embodiments may better maintain carpal spacing and preserve more native tissue when compared to PRC, which involves removal of the proximal carpal row. Moreover, in some embodiments, wrist implant 100 may preserve greater wrist motion when compared to wrist fusion (e.g., four-corner fusion) and radio-carpal fusion. In comparison to typical TWA procedures, use of wrist implant 100 in certain embodiments may preserve more bone tissue, soft issue, and ligamentous structures, for example, by avoiding the need to resect and/or drill into the distal radius or ulna.

Preservation of these tissues is particularly important in some embodiments as it preserves more aggressive surgical options if a patient's condition later worsens. For example, a carpal hemiarthroplasty in accordance with an embodiment of the invention may be later converted to a TWA if desired. This is made possible in this example because the bone tissue needed to support the TWA (e.g., radial bone tissue) was left intact by the carpal hemiarthroplasty. In one embodiment, conversion of wrist implant 100 into a TWA involves replacement of bearing component 140 and articular component 120 with a carpal ball and radius component as described in U.S. Pat. Nos. 7,625,408, 7,628,819, or U.S. Patent Application Publication No. 2010-0076568, while maintaining carpal plate 160.

In some embodiments, preservation of these tissues also allows for the implantation of additional radial and/or ulnar implants which may be desirable to treat other conditions. For example, in one embodiment, a sigmoid notch implant and/or an ulnar head implant may also be implanted in a patient in addition to wrist implant 100. Details of such additional implants are described, for example, in U.S. Pat. Nos. 7,160,331 and 6,302,915, which are each incorporated herein by reference in their entireties.

Figure 6:
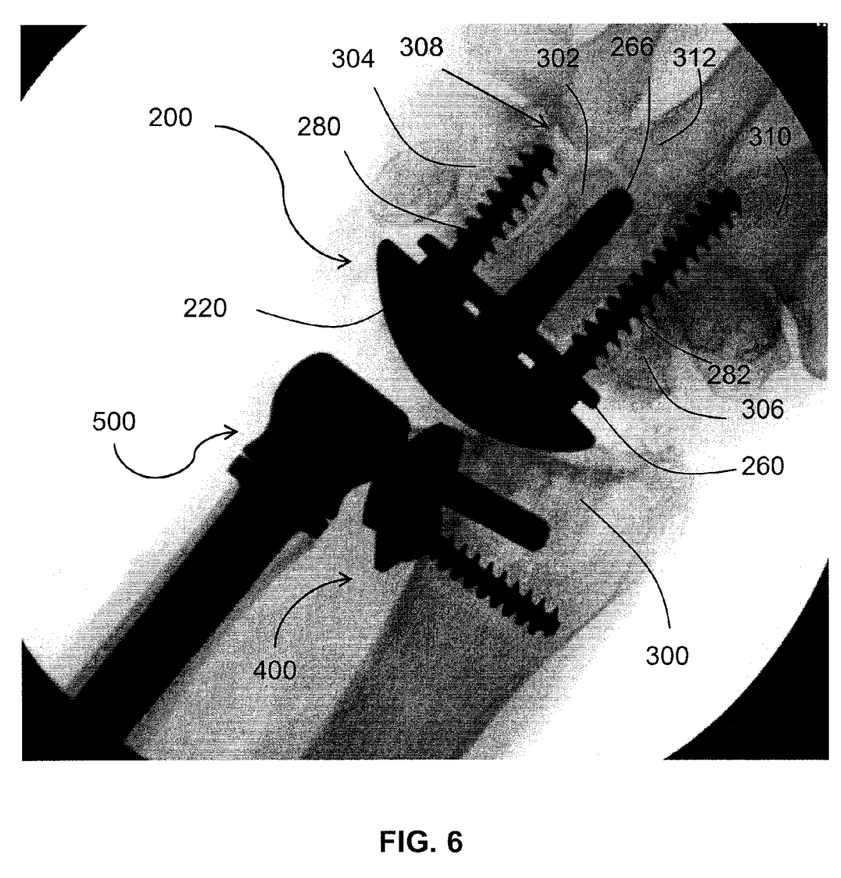
FIG. 6 shows an x-ray image of an implanted wrist implant in accordance with an exemplary embodiment of the present invention.

FIG. 6 shows an x-ray image of an exemplary wrist implant 200 according to an embodiment of the present invention implanted in the wrist of a patient in which the lunate bone and proximal scaphoid bone have been resected. Wrist implant 200 includes an articular component 220 for articulation with the distal end of radius bone 300, a carpal plate 260 having a carpal stem 266, and carpal screws 280 and 282. Carpal stem 266 is inserted into capitate bone 302, bone screw 280 is inserted into hamate bone 304, and bone screw 282 is inserted into the remaining portion of the scaphoid bone 306. Carpal stem 266 does not extend into the third metacarpal 312. More particularly, neither carpal stem 266 nor carpal screw 280 extends into the carpal-metacarpal joint 308. Carpal screw 282, which has a length greater than the length of carpal screw 280, extends into second metacarpal bone 310 in this example. Wrist implant 200 further includes a bearing component disposed between articular component 220 and carpal plate 260, but which is not visible under x-ray imaging. In addition to wrist implant 200, FIG. 6 further shows a sigmoid notch implant 400 implanted into radius bone 300 and an ulnar implant 500.

It should be understood that various changes, substitutions, and alterations can be made herein without departing from the spirit and scope of the invention as defined by the appended claims. It should also be apparent that individual elements identified herein as belonging to a particular embodiment may be included in other embodiments of the invention. Moreover, the scope of the present application is not intended to be limited to the particular embodiments of the process, machine, manufacture, and composition of matter, means, methods and steps described in the specification. As one of ordinary skill in the art will readily appreciate from the disclosure herein, processes, machines, manufacture, composition of matter, means, methods, or steps, presently existing or later to be developed that perform substantially the same function or achieve substantially the same result as the corresponding embodiments described herein may be utilized according to the present invention.

What is claimed is:

1. An implant for carpal hemiarthroplasty comprising:
an articular component having a convex articular surface having a first curvature in a first direction defined by a major radius of curvature and a second curvature in a second direction perpendicular to the first direction defined by a minor radius of curvature, the major radius of curvature being larger than the minor radius of curvature, wherein the convex articular surface is shaped to conform to an unresected distal end of a radius bone such that the first direction corresponds to a ulnar-radial direction and the second direction corresponds to a dorsal-palmar direction, wherein the first curvature is selected to emulate a curve traced by a proximal portion of a scaphoid-lunate complex during normal articulation of a human wrist in radial and ulnar deviation and the second curvature is selected to emulate a curve traced by the proximal portion of the scaphoid-lunate complex during normal articulation of the human wrist in flexion and extension;

a bearing component rigidly fixed to the articular component opposite the convex articular surface and having a bearing surface; and a carpal plate rotatably coupleable to the bearing component having a proximal surface and a distal surface, the proximal surface having a contour substantially conforming to the bearing surface, wherein the articular component defines a concavity opposite the convex articular surface, and wherein the articular component further includes a lip surrounding the concavity;

wherein a proximal portion of the bearing component is received in the concavity, and wherein the bearing component includes a flange abutting the lip; and wherein no component of the implant is configured to be fixed to or inserted into the radius bone and/or an ulna bone.

2. The implant of claim 1, wherein the articular component is configured to articulate with the unresected distal end of a radius bone about two perpendicular axes of rotation.

3. The implant of claim 1, wherein the articular component further includes a ridge extending into the concavity and wherein the bearing component includes a groove for receiving the ridge.

4. The implant of claim 1, wherein the proximal portion of the bearing component includes a dimension equal to a dimension of the concavity.

5. The implant of claim 1, wherein the articular component comprises a metal or metal alloy, and wherein the bearing component comprises a polymer.

6. The implant of claim 5, wherein the articular component comprises a cobalt-chrome alloy and the bearing component comprises ultra high molecular weight polyethylene.

7. The implant of claim 1, wherein the bearing surface has a concave curvature, wherein the proximal surface of the carpal plate has a convex curvature, and wherein the concave curvature of the bearing surface and the convex curvature of the proximal surface are defined by substantially the same radius of curvature.

8. The implant of claim 1, wherein the bearing surface has a concave curvature defined by a radius of curvature larger than the major radius of curvature of the convex articular surface.

9. The implant of claim 1, wherein the carpal plate includes a protrusion extending from the proximal surface, and wherein the bearing component is configured to rotate with respect to the carpal plate about the protrusion.

10. The implant of claim 9, wherein the protrusion includes a spheroidal portion and a support securing the spheroidal portion to the proximal surface of the carpal plate, the spheroidal portion including a diameter larger than a diameter of the support.

11. The implant of claim 9, wherein the bearing component includes a socket opening to the bearing surface for receiving the protrusion therein.

12. The implant of claim 1, further comprising a first carpal screw and a second carpal screw, each screw having a head and a shaft that is at least partially threaded, and wherein the bearing component includes a first cavity for receiving the head of the first carpal screw and a second cavity for receiving the head of the second carpal screw.

13. The implant of claim 12, wherein the first carpal screw and the second carpal screw are engageable with the bearing component to limit the rotational articulation between the bearing component and the carpal plate.

14. The implant of claim 12, wherein the first carpal screw is longer than the second carpal screw.

* * * * *